United States Patent
Baldauf et al.

(10) Patent No.: US 7,723,246 B2
(45) Date of Patent: May 25, 2010

(54) LAMINATE MATERIAL WEB AND METHOD FOR THE PRODUCTION OF A LAMINATE MATERIAL WEB

(75) Inventors: Georg Baldauf, Laer (DE); Marcus Schönbeck, Versmold (DE); Christoph Willing, Vreden (DE)

(73) Assignee: Nordenia Technologies GmbH, Gronau (DE)

( * ) Notice: Subject to any disclaimer, the term of this patent is extended or adjusted under 35 U.S.C. 154(b) by 362 days.

(21) Appl. No.: 11/981,995

(22) Filed: Nov. 1, 2007

(65) Prior Publication Data

US 2008/0108267 A1 May 8, 2008

(30) Foreign Application Priority Data

Nov. 2, 2006 (EP) .................................. 06022799

(51) Int. Cl.
*B32B 27/12* (2006.01)
*B32B 5/26* (2006.01)
*B32B 3/10* (2006.01)

(52) U.S. Cl. ........................ 442/394; 418/114; 418/131; 418/134; 418/136; 442/381; 156/265

(58) Field of Classification Search ................. 442/381, 442/394; 428/114, 131, 134, 136; 156/265
See application file for complete search history.

(56) References Cited

U.S. PATENT DOCUMENTS 5,804,021 A * 9/1998 Abuto et al. ................. 156/252

| 6,461,715 | B1 | 10/2002 | Guenther et al. |
| 6,974,514 | B2 | 12/2005 | Hamulski et al. |
| 7,083,691 | B2 | 8/2006 | Hamulski et al. |
| 2003/0194936 | A1 | 10/2003 | Jackson et al. |
| 2006/0121252 | A1* | 6/2006 | Lightcap et al. ............. 428/192 |
| 2006/0162843 | A1 | 7/2006 | Baldauf et al. |
| 2006/0292328 | A1 | 12/2006 | Baldauf et al. |

FOREIGN PATENT DOCUMENTS

| EP | 1 331 090 | 7/2003 |
| EP | 1 342 562 | 9/2003 |
| EP | 1 686 209 A1 | 8/2006 |
| EP | 1 736 306 | 12/2006 |
| WO | WO 98/16380 | 4/1998 |

\* cited by examiner

*Primary Examiner*—Norca L Torres-Velazquez
(74) *Attorney, Agent, or Firm*—Collard & Roe, P.C.

(57) ABSTRACT

A laminate material web has two webs of nonwoven fabric that lie on the outside, and film strips of an elastic film disposed between them, in sections, whereby the nonwoven fabric webs are connected with one another in the regions between the film strips. The film strips are connected with the inner surfaces of the nonwoven fabric webs only at the two longitudinal edges, in each instance, both on the top and on the bottom, and the nonwoven fabric webs have weakenings running in the web direction, in the regions that cover the film strips. A method for the production of a laminate material web is also described.

10 Claims, 2 Drawing Sheets

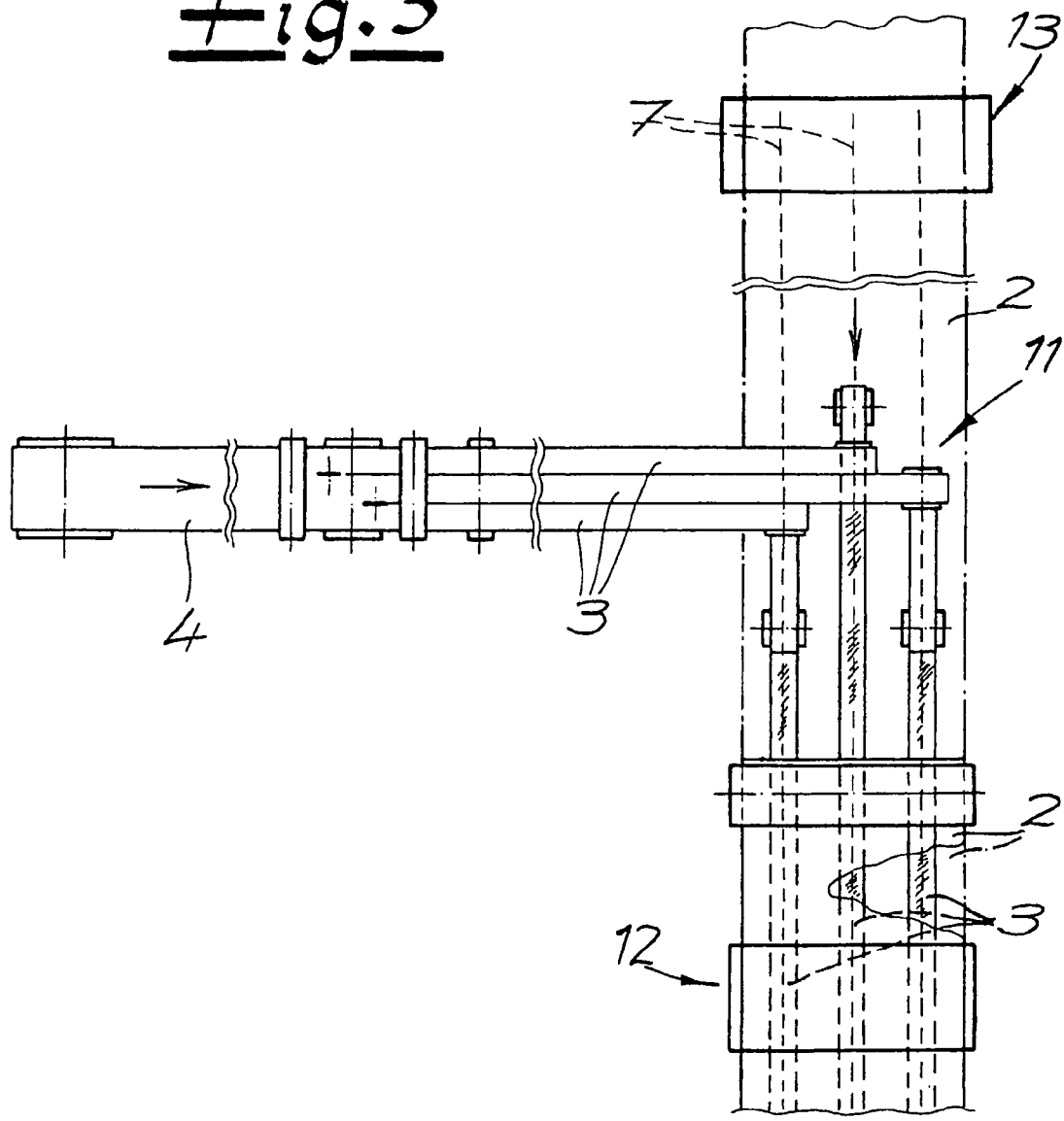

LAMINATE MATERIAL WEB AND METHOD FOR THE PRODUCTION OF A LAMINATE MATERIAL WEB

CROSS REFERENCE TO RELATED APPLICATIONS

Applicants claim priority under 35 U.S.C. §119 of European Application No. 06 022 799.8 filed Nov. 2, 2006.

BACKGROUND OF THE INVENTION

1. Field of the Invention

The present invention relates to a laminate material web having two webs of nonwoven fabric that lie on the outside, and film strips of an elastic film disposed between them, in sections. The nonwoven fabric webs are connected with one another in the regions between the film strips.

The laminate material web can be used, for example, for the production of elastic closure strips for baby diapers or adult diapers, which closure strips can also have the shape of diaper ears, and possess an elastic center region as well as less elastic end sections that follow the former on both sides. The non-elastic or less elastic end regions are utilized in order to attach closure elements, e.g. hook tapes, and to affix the closure strip on the diaper chassis. For cost-advantageous production, a large number of elastic film strips is laminated in between two broad webs of nonwoven fabric, at a distance from one another. The closure strips needed for diaper production are then cut from the resulting laminate material web.

2. The Prior Art

A laminate material web having the characteristics described initially is known from the reference EP 1 686 209 A1. Here, the film strips have an elastic, tacky core, which is covered with a thin nonwoven layer on one or both sides, in order to allow processing of the film strips despite the tackiness of the core. To guarantee the desired elasticity of the laminate material webs, these webs are subjected to a ring rolling process. In this way, distortions form in the stretched and not elastically resilient nonwoven fabric webs, which are pulled smooth in a stretching process.

A simple possibility for the production of a laminate material web having the desired properties consists in connecting two nonwoven fabric strips with one another by means of an elastic film. However, the asymmetrical structure of such a laminate tends to tear off in the region of the connection between film and nonwoven fabric web, which is generally produced by means of adhesive. Furthermore, it is disadvantageous that the elastic film is exposed in this case, and therefore the laminate material web does not possess the pleasant textile character of the remainder of the diaper surface in this region.

SUMMARY OF THE INVENTION

It is an object of the invention to provide a laminate material web for the production of closure elements for diapers, particularly adult diapers, which is easy to produce and, at the same time, possesses sufficiently great stability.

Proceeding from a laminate material web having the characteristics described initially, these and other objects are achieved, according to the invention, by connecting the film strips with the inner surfaces of the nonwoven fabric webs only at the two longitudinal edges, in each instance, both on the top and on the bottom, and by providing the nonwoven fabric webs with a weakening running in the web direction in the regions that cover the film strips. The weakening can be configured as a perforation. Alternatively or in addition, the weakening can be configured as a slitting or cutting. A very stable laminate is achieved by the two-sided connection of the film strip with the nonwoven fabric webs that lie on the outside, which laminate easily withstands the stresses of a diaper closure element. If one stretches the laminate material web according to the invention in the crosswise direction, the weakening tears, and the elastic film strip is exposed. Thus, the elasticity of the film strip can be fully utilized. First-time stretching of the diaper closure element provided with the weakening is generally performed by the person putting the diaper on; in the case of adult diapers, this person would be the diaper wearer himself/herself, if applicable.

Preferably, the laminate material webs have one weakening per film strip, in each instance, and the weakenings run symmetrical to the film strip, in each instance. It is practical if the weakenings extend over the entire length of the film strips. For the production of non-elastic sections, the nonwoven fabric webs can be glued to one another in the regions between the film strips. It is practical if the edge regions of the film strips are also glued to the inner surfaces of the nonwoven fabric webs. In both cases, hot-melt glues can be used as adhesives; they produce the laminate by means of a lamination process.

In order to retain a textile character of the diaper closure element over the entire surface even after the elastic film strip has been exposed, the film strips can consist, in each instance, of an elastomer layer and at least one outer layer of nonwoven fabric applied to the elastomer layer. Because the elastomer layer is frequently tacky, it can be practical to provide it with outer layers of nonwoven fabric on both sides. The nonwoven fabric outer layers can have a significantly lesser thickness than the nonwoven fabric webs, in order to fulfill their intended functions, in other words textile character on the one hand, and coverage of the tacky elastomer layer, on the other hand.

In another aspect, a method for the production of a laminate material web is provided whereby film strips are produced from an elastic film by means of a cutting process, whereby the film strips are then disposed between nonwoven fabric webs, in sections, and whereby afterwards the nonwoven fabric webs are connected with one another in the region between the film strips. The film strips are connected with the inner surfaces of the nonwoven fabric webs only at the two longitudinal edges, in each instance, both on the top and on the bottom, and the nonwoven fabric webs are weakened into the regions that cover the film strips, in the web direction. Practical embodiments of this method are described below.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 3 shows a method according to the invention for the production of a laminate material web.

DETAILED DESCRIPTION OF PREFERRED EMBODIMENTS

Figure 1:
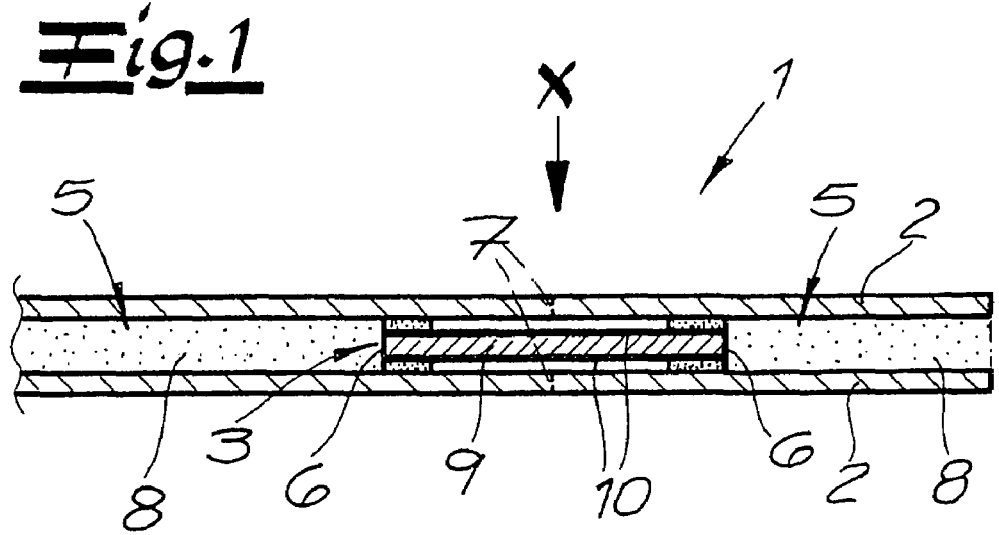
FIG. 1 is a schematic cross-sectional representation of a diaper closure element produced from a laminate material web according to the invention.
Figure 2:
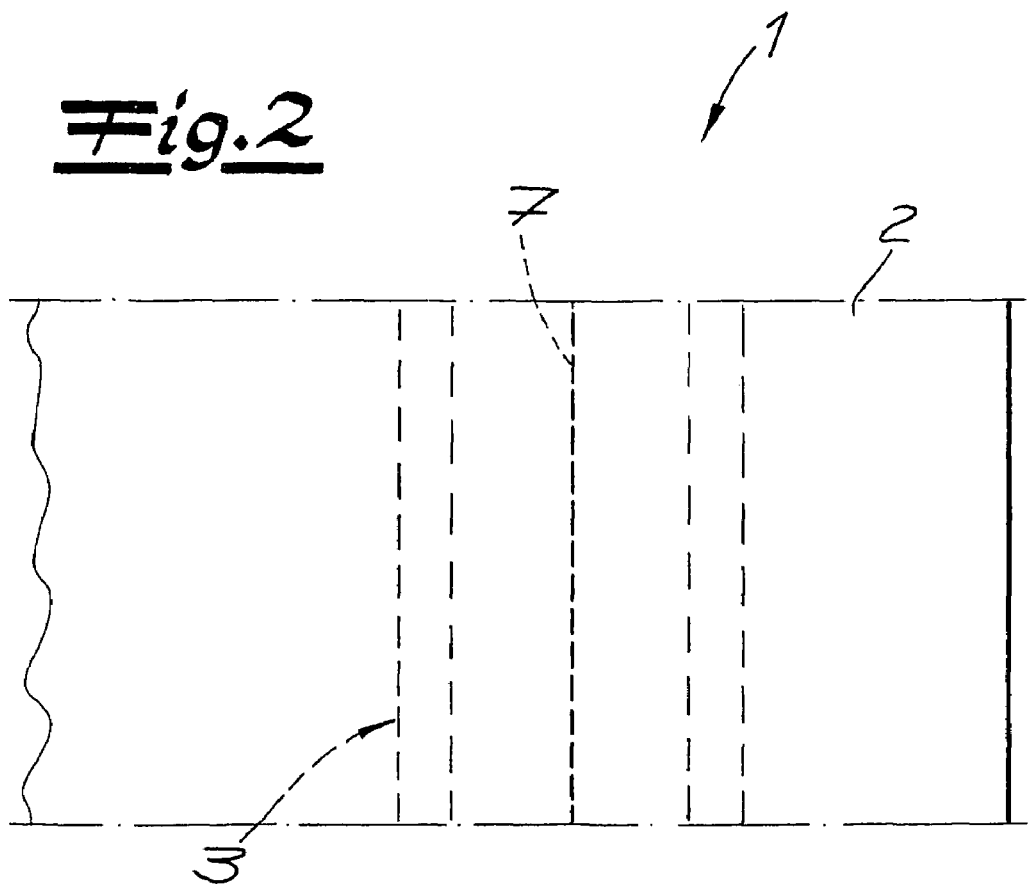
FIG. 2 is a top view X in FIG. 1.

Referring now in detail to the drawings FIG. 1 shows a laminate material web from which individual diaper closure elements 1 can be produced. The laminate material web has two nonwoven fabric layers 2 that lie on the outside, and film strips 3 of an elastic film 4 that are disposed between them, in sections (see FIG. 3). Nonwoven fabric webs 2 are connected with one another in the regions 5 between film strips 3. Film strips 3 are connected only with the inner surfaces of nonwoven fabric webs 2 at the two longitudinal edges 6, in each instance, both on the top and on the bottom.

Nonwoven fabric webs 2 have weakenings 7 running in the web direction, in the regions that cover film strips 3, which are configured as perforations in the exemplary embodiment. In this connection, nonwoven fabric webs 2 possess one perforation 7 per film strip 3, in each instance, which in turn runs symmetrically to film strip 3. Perforations 7 extend over the entire length of film strips 3.

In regions 5 between film strips 3, nonwoven fabric webs 2 are glued to one another over their full area, while the edge regions of film strips 3 are glued to the inner surfaces of nonwoven fabric webs 2 over their full area. The gluing can be performed using a hot-melt glue 8, within the framework of a lamination process, for example.

It can further be seen from FIG. 1 that film strips 3 consist, in each instance, of an elastomer layer 9 and at least one outer layer 10 of nonwoven fabric that is applied to elastomer layer 9. In the exemplary embodiment, elastomer layer 9 is tacky and therefore provided with thin outer layers 10 of nonwoven fabric on both sides. It is practical if these outer layers 10 have a weight per area unit between 5 g/m$^2$ and 15 g/m$^2$, whereas nonwoven fabric webs 2 have a clearly higher weight per area unit, in each instance.

FIG. 3 shows a method according to the invention, for the production of a laminate material web. First, film strips 3 are produced from an elastic film 4, by a cutting process; these strips are guided over deflection devices 11 and passed to a lamination device 12 as parallel strips, spaced apart from one another; in the lamination device, film strips 3 are disposed between nonwoven fabric webs 2, in sections, and laminated in. Nonwoven fabric webs 2 are connected with one another via a full-area adhesive application in the regions 5 between film strips 3. Film strips 3 are connected with the inner surfaces of nonwoven fabric webs 2 via a corresponding adhesive application on the inner surface of the two laminate material webs 2, only at the two longitudinal edges 6, both on the top and on the bottom. Both the connection of the two nonwoven fabric webs 2 and the connection of the film strips 3 with the two nonwoven fabric webs 2 takes place in the lamination direction. Before that connection, nonwoven fabric webs 2 are perforated in the regions that cover film strips 3, symmetrically to film strip 3, in each instance, in the web direction. For this purpose, nonwoven fabric webs 2 pass through a corresponding perforation device 13. The laminate material web that is produced can be processed further to produce elastic diaper closures 1, which have only one film strip 3, in each instance, using appropriate cutting processes.

Nonwoven fabric webs 2 that have been connected with one another form non-elastic regions in regions 5 between film strips 3. The sections that contain a film strip 3, in each instance, form an elastic region that can be exposed. It is practical if nonwoven fabric webs 2 and outer layers 10 of film strips 3 are made up of the same raw materials, for example polypropylene fibers. With regard to the fiber structure, outer layers 10 of film strips 3 can differ from nonwoven fabric webs 2. It is practical if a dense fiber structure is selected for outer layers 10 of film strips 3, which prevents the layers from sticking together when they have been wound up into a roll. However, a comparatively thin outer layer thickness is sufficient to guarantee the desired textile surface. It is practical if nonwoven fabric webs 2 that are laminated onto the outside, on the other hand, are clearly thicker than outer layers 10.

Although only a few embodiments of the present invention have been shown and described, it is to be understood that many changes and modifications may be made thereunto without departing from the spirit and scope of the invention as defined in the appended claims.

What is being claimed is:

1. A laminate material web comprising
  (a) first and second outside nonwoven fabric webs, each nonwoven fabric web having an inner surface; and
  (b) a plurality of elastic film strips disposed between said nonwoven fabric webs in sections, each film strip having first and second longitudinal edges;
  wherein said nonwoven fabric webs are connected with one another in regions between said film strips;
  wherein each film strip is connected with the inner surfaces of said nonwoven fabric webs only at respective first and second longitudinal edges both on a top portion and on a bottom portion of each longitudinal edge; and
  wherein the nonwoven fabric webs have weakings extending in a web direction in regions covering the film strips.

2. The laminate material web according to claim 1, wherein the nonwoven fabric webs have one weakening per film strip, in each instance, and the weakenings extend symmetrically to the respective film strip.

3. The laminate material web according to claim 1, wherein each weakening extends over an entire length of the respective film strips.

4. The laminate material web according to claim 1, wherein the nonwoven fabric webs are glued to one another in the regions between the film strips.

5. The laminate material web according to claim 1, wherein the edge regions of the film strips are glued to the inner surfaces of the nonwoven fabric webs.

6. The laminate material web according to claim 1, wherein each film strip comprises an elastomer layer and at least one outer layer of nonwoven fabric applied to the elastomer layer.

7. The laminate material web according to claim 6, further comprising first and second outer layers of nonwoven fabric provided on each side of the elastomer layer.

8. A method for producing a laminate material comprising the steps of:
  (a) producing a plurality of film strips from an elastic film using a cutting process;
  (b) subsequently disposing the film strips between first and second nonwoven fabric webs in sections; and
  (c) afterwards connecting the nonwoven fabric webs with one another in regions between the film strips;
  wherein each film strip is connected with inner surfaces of the nonwoven fabric webs only at first and second longitudinal edges of the film strip at a top portion and at a bottom portion of the longitudinal edges; and
  wherein the nonwoven fabric webs are weakened in regions covering the film strips in a web direction.

9. The method according to claim 8, wherein the nonwoven fabric webs are weakened once per film strip, in each instance, symmetrically to the film strip.

10. The method according to claim 8, wherein the nonwoven fabric webs are glued to one another in the region between the film strips, and the edge regions of the film strips are glued to the inner surfaces of the nonwoven fabric webs.

* * * * *